(12) United States Patent
Barrett et al.

(10) Patent No.: US 11,617,683 B2
(45) Date of Patent: Apr. 4, 2023

(54) TREATMENT LASER WITH REFLEX MIRROR

(71) Applicant: Ellex Medical Pty Ltd, Mawson Lakes (AU)

(72) Inventors: Bradley Barrett, Mawson Lakes (AU); David Haarhoff, Mawson Lakes (AU); Timothy Dixon, Mawson Lakes (AU)

(73) Assignee: ELLEX MEDICAL PTY LTD, Mawson Lakes (AU)

( * ) Notice: Subject to any disclaimer, the term of this patent is extended or adjusted under 35 U.S.C. 154(b) by 509 days.

(21) Appl. No.: 16/341,690

(22) PCT Filed: Oct. 11, 2017

(86) PCT No.: PCT/AU2017/051100
§ 371 (c)(1),
(2) Date: Apr. 12, 2019

(87) PCT Pub. No.: WO2018/068089
PCT Pub. Date: Apr. 19, 2018

(65) Prior Publication Data
US 2019/0282403 A1 Sep. 19, 2019

(30) Foreign Application Priority Data
Oct. 14, 2016 (AU) .................................. 2016904179

(51) Int. Cl.
*A61F 9/008* (2006.01)
(52) U.S. Cl.
CPC ...... *A61F 9/00825* (2013.01); *A61F 9/00821* (2013.01); *A61F 2009/0087* (2013.01);
(Continued)

(58) Field of Classification Search
CPC .... A61F 2009/00868; A61F 2009/0087; A61F 2009/00891; A61F 9/00825; A61F 9/00821
See application file for complete search history.

(56) References Cited

U.S. PATENT DOCUMENTS 8,876,808 B2 11/2014 Feklistov et al.
9,060,846 B2 6/2015 Feklistov et al.
(Continued)

FOREIGN PATENT DOCUMENTS

EP 2384727 A1 11/2011
WO WO 2018/068089 A1 4/2018

OTHER PUBLICATIONS

PCT/AU2017/051100 International Search Report and Written Opinion dated Jan. 2, 2018.
(Continued)

*Primary Examiner* — Lynsey C Eiseman
*Assistant Examiner* — Amanda L Steinberg
(74) *Attorney, Agent, or Firm* — Alston & Bird LLP

(57) ABSTRACT

An ophthalmic laser system for generating a first beam at a first wavelength on a first beam path and a second beam at a second wavelength on a second beam path, and directing optics to selectively direct the first beam or the second beam to a treatment beam path. The ophthalmic laser system incorporates a reflex coaxial illuminator comprising a reflex mirror movable on an axis from a position out of the treatment beam path to a position in the treatment beam path to direct illumination into an illumination path coaxial with the treatment beam path. The reflex mirror is adapted to transmit a beam that follows the second beam path.

12 Claims, 3 Drawing Sheets

(52) U.S. Cl.
CPC ............... *A61F 2009/00868* (2013.01); *A61F 2009/00887* (2013.01); *A61F 2009/00891* (2013.01)

(56) References Cited

U.S. PATENT DOCUMENTS

| | | | |
|---|---|---|---|
| 10,369,051 B2 | 8/2019 | Plunkett et al. | |
| 10,898,378 B2 | 1/2021 | Plunkett et al. | |
| 2007/0222945 A1* | 9/2007 | Tsukada | A61B 3/102 |
| | | | 351/205 |
| 2010/0152716 A1 | 6/2010 | Previn et al. | |
| 2010/0215066 A1 | 8/2010 | Mordaunt et al. | |
| 2014/0135753 A1* | 5/2014 | Feklistov | A61F 9/00823 |
| | | | 606/6 |
| 2015/0141973 A1 | 5/2015 | Feklistov et al. | |
| 2015/0148786 A1* | 5/2015 | Plunkett | F21V 14/04 |
| | | | 606/4 |
| 2015/0157506 A1 | 6/2015 | Feklistov et al. | |
| 2015/0335479 A1* | 11/2015 | Shibata | A61F 9/009 |
| | | | 606/4 |
| 2016/0166319 A1* | 6/2016 | Yu | H01S 3/109 |
| | | | 606/3 |
| 2018/0235462 A1* | 8/2018 | Gooi | A61B 3/102 |
| 2018/0368915 A1 | 12/2018 | Xia et al. | |
| 2019/0209371 A1 | 7/2019 | Plunkett et al. | |
| 2019/0282403 A1 | 9/2019 | Barrett et al. | |
| 2020/0046553 A1 | 2/2020 | Barrett et al. | |
| 2021/0128348 A1 | 5/2021 | Xia et al. | |

OTHER PUBLICATIONS

PCT/AU2017/051100 International Preliminary Report on Patentability dated Apr. 16, 2019.
EP 17859819 Supplemental European Search Report dated Mar. 17, 2020.

* cited by examiner

TREATMENT LASER WITH REFLEX MIRROR

CROSS-REFERENCE TO RELATED APPLICATIONS

This application is the US national stage of PCT/AU2017/051100 filed Oct. 11, 2017, which claims the benefit of Australian Provisional Application No. 2016904179 filed Oct. 14, 2016.

FIELD OF THE INVENTION

The present invention relates to the field of ophthalmic lasers. More particularly, the invention relates to maintaining safety of users of ophthalmic laser systems.

BACKGROUND TO THE INVENTION

The Applicant has previously described an Ophthalmic Laser System that is useful for performing selective laser trabeculoplasty (SLT) and secondary cataract surgery procedures. The laser system is described in International Patent Application Number PCT/AU03/01224. The laser system generates a first beam at a wavelength suitable for performing cataract surgery procedures and selectively generates a second beam at a wavelength suitable for performing SLT. Each beam may be selected using an extracavity deflection means to direct the beam down a selected beam path.

It is important in ophthalmic treatments for the ophthalmologist to be able to view the treatment zone for as long as possible during the treatment. The Applicant has developed a reflex coaxial illuminator that utilises a flip mirror that only intercepts the viewing path for the short period of the laser treatment. The invention is described in International Patent Application number PCT/AU2013/000546.

It would be desirable for all ophthalmic laser systems to be able to benefit from the reflex coaxial illuminator safety benefits. However, there are a number of problems to be addressed when looking to implement the reflex coaxial illuminator on the ophthalmic laser system described above. When operating in secondary cataract surgery mode the system must:
  illuminate the retina at the best possible angle (which is co-axial); allow the aiming beams to pass;
  allow the treatment beam to pass; and
  there should be no interference to the viewing path of the ophthalmologist.
  When operating in SLT mode the system must:
  provide adequate illumination to the anterior of the eye;
  allow the aiming beam to pass;
  allow the treatment beam to pass; and
  there should be no interference to the viewing path of the ophthalmologist.

There is a need to find a solution that allows the SLT aiming beam to pass while providing adequate illumination.

SUMMARY OF THE INVENTION

In one form, although it need not be the only or indeed the broadest form, the invention resides in an ophthalmic laser system comprising:
  a laser module producing a beam of short pulses of radiation with high energy density at a first wavelength;
  a first beam path incorporating optical elements for directing the beam at said first wavelength into a treatment beam path to an eye of a patient;
  a second beam path incorporating a frequency doubling module that converts the beam at the first wavelength to a beam at a second wavelength, and optical elements for directing the beam at said second wavelength to the treatment beam path;
  means for selectively deflecting the beam at said first wavelength into the second beam path, said means being operable between a first position in which the beam at said first wavelength follows the first beam path and a second position in which the beam at said first wavelength is deflected to said second beam path; and
  a reflex coaxial illuminator comprising a reflex mirror movable on an axis from a position in the treatment beam path to a position out of the treatment beam path;
  wherein the reflex mirror is adapted to transmit a beam that follows the second beam path.

In one form the reflex mirror has a central aperture that a beam following the second beam path passes through.

In another form the reflex mirror is dichroic mirrors that transmit at the wavelength of beams following the second beam path. Suitably the dichroic mirror is formed from a pair of dichroic mirrors arranged back to back so that any deflection caused by one mirror is corrected by the other mirror.

The beams that follow the second beam path may be an aiming beam and/or a treatment beam.

Further features and advantages of the present invention will become apparent from the following detailed description.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION OF THE INVENTION

Figure 1:
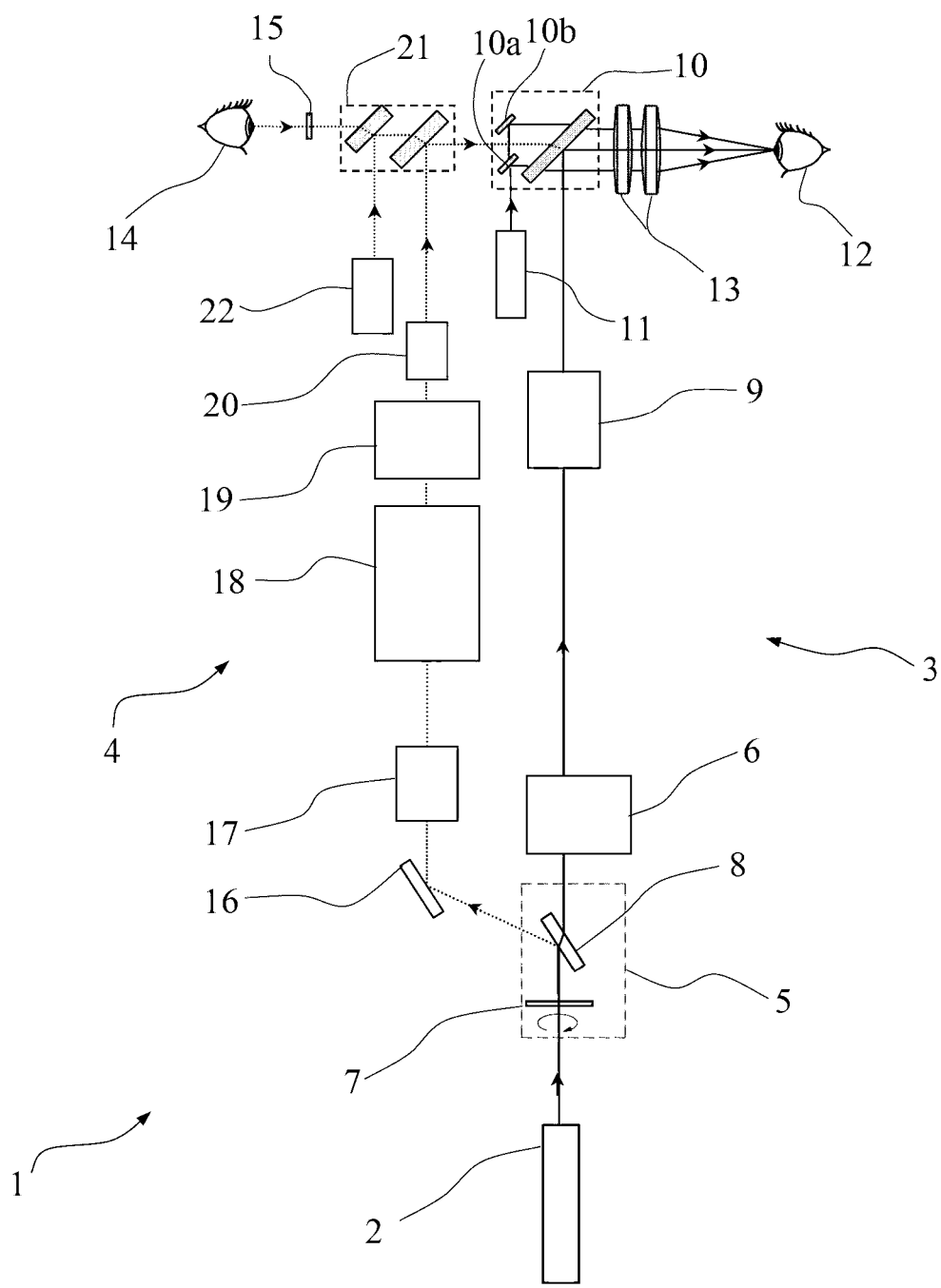
FIG. 1 is a schematic of an ophthalmic laser system including a photodisruptor for treatment of secondary cataracts and an SLT optical system for treatment of glaucoma.

Embodiments of the present invention reside primarily in an ophthalmic laser system incorporating a reflex coaxial illuminator. Accordingly, the elements have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

As described in PCT/AU03/01224, FIG. 1 shows an embodiment of an ophthalmic laser system 1 useful for treating glaucoma and secondary cataracts. The system is comprised of a laser module 2, a photodisruptor optical system 3 and SLT optical system 4.

A pulsed beam from the laser module 2 is attenuated at attenuator/beam steering module 5. An energy monitor system 6 measures the energy in each pulse. A half wave plate 7 within the attenuator/beam steering module 5 is adjusted to regulate the intensity of the pulsed beam in the photodisruptor optical system 3. A polarizing plate 8 may deflect the pulsed beam to the SLT optical system 4 depending on the orientation of the half wave plate 7.

Beam shaping optical module 9 expands the pulsed beam before it travels up to the folding mirror module 10. The expanded beam is then focused by objective lens 13 to produce an 8-10 µm beam waist at the treatment site which is required to produce photodisruption. An aiming laser module 11 provides a continuous, visible laser beam that is split into two beams and deflected by folding mirror module 10 to give a targeting reference for the treatment beam. These two aiming laser beams converge with the pulsed treatment beam at the target site in a patient's eye 12 via objective lens 13. An operator 14 views the patient's eye 12 through the folding mirror module 10. A safety filter 15 protects the eye of the operator. The folding mirrors 10a, 10b are positioned so that the viewing axis of the operator is not impeded.

The SLT optical system 4 comprises a mirror 16 that directs a deflected pulsed beam from the polarizing plate 8 in the attenuator/beam steering module 5 to the frequency doubling module 17. In one embodiment the frequency doubling module 17 converts the output of the laser module (such as Nd:YAG at 1064 nm) to twice the wavelength so that the output of the SLT optical system is in the visible spectrum. The visible pulsed beam is effective in treating glaucoma in patients.

The pulsed visible beam may be attenuated at the SLT attenuator 18 to regulate the energy in the pulsed visible beam. An energy monitor system 19 measures the energy in each pulse.

A beam shaping module 20 adjusts the beam profile to provide an even energy distribution at the treatment plane. The visible beam then travels to a second folding mirror module 21. A second aiming laser module 22 provides a single aiming laser beam which is deflected by the second folding mirror 21 and transmitted through folding mirror module 10 and objective lens 13. The continuous visible laser aiming beam generated by the second aiming laser module 22 coincides with the pulsed visible beam at the target site in a patient's eye 12 via objective lens 13.

Figure 2:
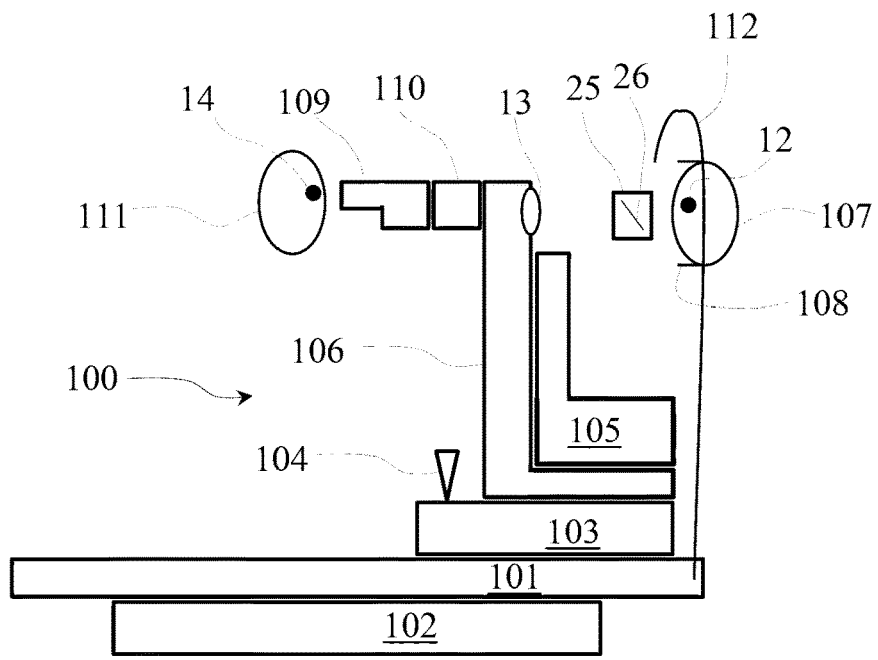
FIG. 2 is a schematic of the ophthalmic laser system of FIG. 1 embodied in a slit lamp assembly.

The ophthalmic laser system 1 is conveniently integrated into a slit lamp assembly 100, as shown in FIG. 2. The slit lamp assembly 100 consists of a table 101 with components of the system arranged in a console 102 located beneath the table 102. A slit lamp base 103 is movable on the table 101 using a joystick 104. The slit lamp 105 and the laser delivery head 106 are located on the console base 103 and move with it. The eye 12 of the patient 107 is fixed by the patient 107 resting on a chin rest 108 that is attached to the table 101.

Binoculars 109 and magnification changer 110 are provided for viewing by the ophthalmologist 111.

The optical path for the ophthalmologist 111 is from the eye 14, through binoculars 109, magnification changer 110 and objective lens 13 to the eye 12 of the patient 107. The laser path is through the laser delivery head 106 and objective lens 13 to the eye 12. The aiming beam path is also through the laser delivery head 106 and objective lens 13 to the eye 12. A fixation lamp 112 provides illumination directly to the eye 12.

In order to provide illumination to the eye 12 coaxial with the laser treatment beams the arrangement shown in FIG. 1 is varied to include a reflex coaxial illuminator of the type described in International Patent Application number PCT/AU2013/000546. A reflex coaxial illuminator 25 comprises a reflex mirror 26 that directs light from the slit lamp 105 to the eye 12. As with the prior art, the light source 105 is suitably a broad spectrum (white) light source.

Figure 3:
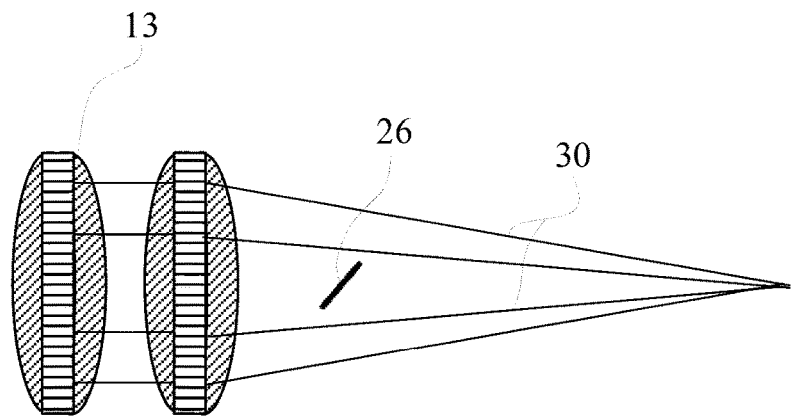
FIG. 3 shows the position of a reflex coaxial illuminator in the path of the photodisruptor.
Figure 4:
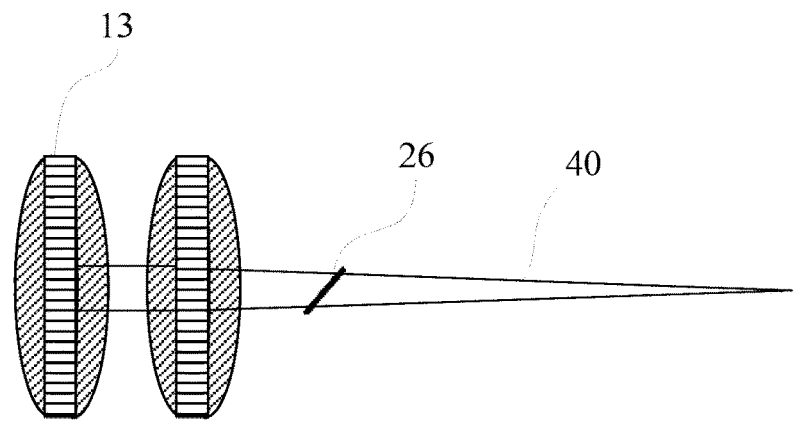
FIG. 4 shows the position of a reflex coaxial illuminator in the path of the SLT optical system.

As shown in FIG. 3, the mirror 26 is of a size and shape to be located between the pair of aiming beams 30 from the aiming laser 11 that are directed to the eye 12 by the objective lens 13. The user positions the aiming beams 30 by moving the slit lamp 105 to target a treatment zone while viewing the eye through binoculars 109. As shown in FIG. 4, the mirror 26 is in the path of the aiming beam 40 from the aiming laser 22.

Figure 5:
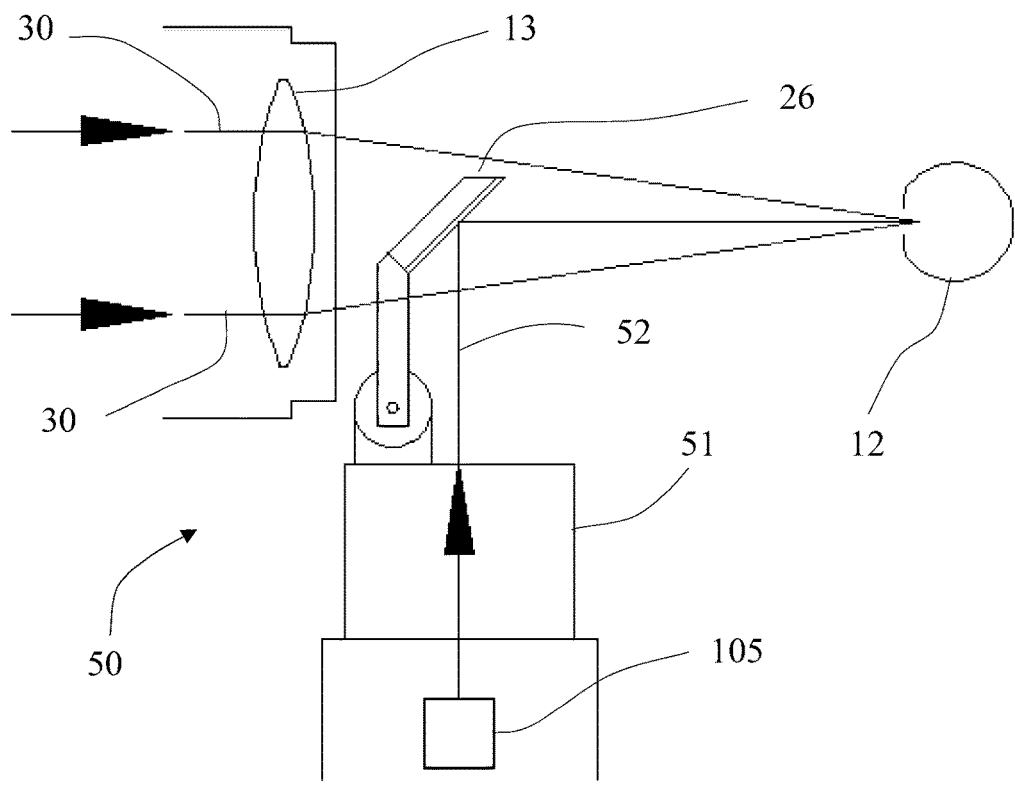
FIG. 5 shows the details of a reflex coaxial illuminator.

As described in International Patent Application number PCT/AU2013/000546 and shown in FIG. 5 the reflex coaxial illuminator 25 includes an actuator 51 to flip the mirror 26 out of the beam path when required but otherwise direct the slit lamp illumination 52 to the eye of the patient. However, for the laser system of FIG. 1 an additional solution is required since there are five separate beams that must be able to reach the eye while continuing to allow the physician to observe the treatment zone. The five beams are the slit lamp illumination 52, the photodisruptor aiming beams 30, the beam from the photodisruptor laser 3, the SLT aiming beam 40, and the beam from the SLT laser 4.

Furthermore, the ophthalmic laser described by reference to FIG. 1 may operate in either photodisruptor mode utilizing the laser beam along the beam path shown in photodisruptor optical system 3 or in SLT mode utilizing the laser beam along the beam path shown in SLT optical system 4.

In photodisruptor mode the requirements are:
Provide illumination the retina as close to co-axial as possible;
Allow the aiming beams to pass;
Allow the treatment beam to pass;
Not interfere with viewing by the user.

In SLT mode the requirements are:
Provide illumination to the anterior of the eye;
Allow the aiming beam to pass;
Allow the treatment beam to pass;
Not interfere with viewing by the user.

Figure 6:
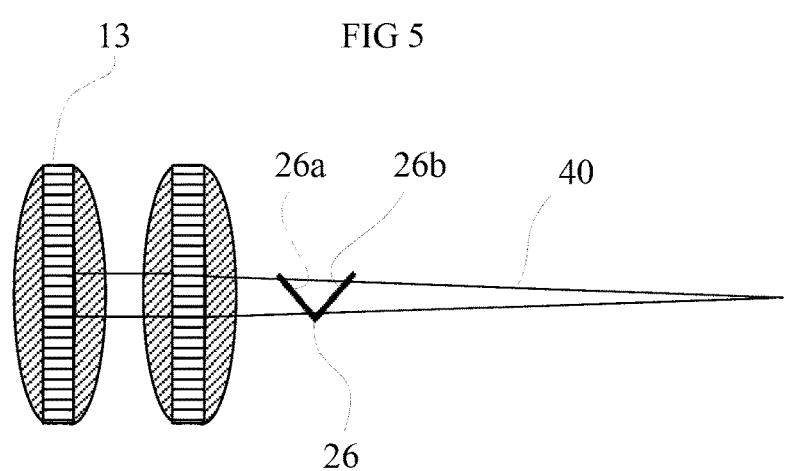
FIG. 6 shows a first embodiment of the invention.

A first embodiment to address the requirements is shown in FIG. 6. In FIG. 6 the mirror 26 is replaced with a pair of dichroic mirrors 26a, 26b arranged to compensate for deviation of the beam path due to refraction that occurs when the aiming beam or SLT beam passes through each mirror 26a, 26b.

The mirrors 26a, 26b are fixed in position relative to each other so as to form a single mirror 26 that passes the aiming laser beam and SLT beam but reflect the illumination from the slit lamp. The mirror 26 is flipped out of the beam path for treatment by the photodisruptor beam.

Figure 7:
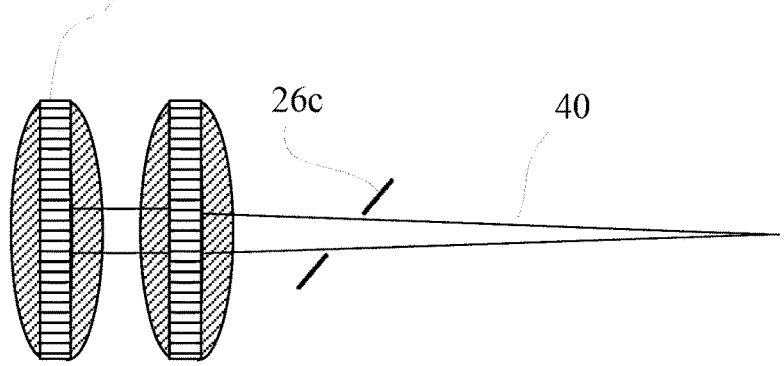
FIG. 7 shows a second embodiment of the invention.

A second embodiment to address the requirements is shown in FIG. 7. In FIG. 7 the mirror 26c is slotted to allow the SLT aiming and treatment beams to pass through while the illumination from the slit lamp is directed to the eye. The binocular viewing path allows viewing while the mirror is in place but the mirror 26c is flipped out of the beam path during operation in the photodisruptor mode.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present invention that have been discussed herein, and other embodiments that fall within the spirit and scope of the above described invention.

The invention claimed is:

1. An ophthalmic laser system comprising:
a laser module configured to produce a beam of pulses of radiation with an energy density at a first wavelength;
a first beam path incorporating optical elements configured to direct the beam at the first wavelength into a treatment beam path to an eye of a patient;
a second beam path incorporating a frequency conversion module configured to convert the beam at the first wavelength to a beam at a second wavelength, and optical elements configured to direct the beam at the second wavelength to the treatment beam path;
an aiming laser producing an aiming beam configured to provide a targeting reference for the beam at the second wavelength;
means configured to selectively deflect the beam at the first wavelength into the second beam path, the means being operable between a first position in which the beam at the first wavelength follows the first beam path and a second position in which the beam at the first wavelength is deflected to the second beam path; and
a reflex coaxial illuminator comprising a reflex mirror movable on an axis from a position in the treatment beam path to a position out of the treatment beam path;
wherein the reflex mirror is adapted to transmit a beam that follows the second beam path and to transmit the aiming beam, and wherein the reflex mirror is a beam splitter that is configured to transmit at the wavelength of the beam following the second beam path and the wavelength of the aiming beam, wherein the beam splitter is formed from a pair of beam splitters arranged back to back, wherein the beam at the second wavelength and the aiming beam pass through each beam splitter, so that any deflection caused by one beam splitter is corrected by the other beam splitter.

2. The ophthalmic laser system of claim 1 wherein the pair of beam splitters is formed from a pair of dichroic mirrors arranged back to back so that any deflection caused by one mirror is corrected by the other mirror.

3. The ophthalmic laser system of claim 1 wherein the laser module is a flashlamp pumped, solid state laser.

4. The ophthalmic laser system of claim 1 wherein the laser module is a Nd:YAG laser configured to produce the beam at the first wavelength at a wavelength of 1064 nm, and wherein the frequency conversion module comprises a frequency doubling module configured to produce the beam at the second wavelength frequency-doubled to 532 nm.

5. The ophthalmic laser system of claim 1 wherein the aiming laser is further configured to provide the targeting reference for the beam at the first wavelength.

6. The ophthalmic laser system of claim 1 further comprising beam steering optics, wherein the beam steering optics comprise a half wave plate and polarizer.

7. The ophthalmic laser system of claim 1 wherein the frequency conversion module comprises a potassium titanyl phosphate (KTP) doubling crystal.

8. The ophthalmic laser system of claim 1 wherein the reflex mirror is rotated about the axis to move from the position in the treatment laser beam to the position out of the treatment laser beam.

9. The ophthalmic laser system of claim 1 wherein the reflex mirror is translated along the axis to move from the position in the treatment laser beam path to the position out of the treatment laser beam path.

10. The ophthalmic laser system of claim 1 wherein the reflex mirror is biased to maintain a position in the treatment laser beam path but is movable to a position out of the treatment laser beam path by an actuator.

11. The ophthalmic laser system of claim 1 wherein the reflex mirror is moved from a position in a treatment laser beam path to a position out of the treatment laser beam path and back without noticeable interruption to viewing by a user.

12. The ophthalmic laser system of claim 1 for selective treatment of glaucoma and secondary cataract, wherein:
the laser module comprises a Q-switched laser which operates to produce pulsed radiation at a first wavelength;
the first beam path is adapted to treating secondary cataract incorporating optical elements comprising an attenuator, beam shaping optics, and directing optics configured to direct a beam of short pulses at the first wavelength along the treatment beam path to an eye of a patient with secondary cataract;
the second beam path is adapted to treating glaucoma by selective laser trabeculoplasty incorporating optical elements comprising an attenuator, and directing optics configured to direct the pulsed beam at the second wavelength along the treatment beam path to an eye of a patient with glaucoma; and
wherein the reflex mirror is configured to direct illumination into an illumination path coaxial with the treatment beam path.

* * * * *